(12) United States Patent
Craig et al.

(10) Patent No.: US 9,993,393 B2
(45) Date of Patent: Jun. 12, 2018

(54) DENTAL COMPOSITIONS AND INITIATOR SYSTEMS WITH POLYCYCLIC AROMATIC COMPONENT

(75) Inventors: Bradley D. Craig, Cottage Grove, MN (US); Brian A. Shukla, Woodbury, MN (US); Joel D. Oxman, Minneapolis, MN (US); Victoria A. Russell, Brooklyn Park, MN (US)

(73) Assignee: 3M INNOVATIVE PROPERTIES COMPANY, St Paul, MN (US)

( * ) Notice: Subject to any disclaimer, the term of this patent is extended or adjusted under 35 U.S.C. 154(b) by 415 days.

(21) Appl. No.: 12/159,250

(22) PCT Filed: Dec. 22, 2006

(86) PCT No.: PCT/US2006/049249
§ 371 (c)(1),
(2), (4) Date: Jun. 26, 2008

(87) PCT Pub. No.: WO2007/079070
PCT Pub. Date: Jul. 12, 2007

(65) Prior Publication Data
US 2009/0005469 A1    Jan. 1, 2009

Related U.S. Application Data

(60) Provisional application No. 60/754,952, filed on Dec. 29, 2005.

(51) Int. Cl.
*A61K 6/00*    (2006.01)
*A61K 6/08*    (2006.01)
*A61K 6/083*   (2006.01)

(52) U.S. Cl.
CPC .......... *A61K 6/0052* (2013.01); *A61K 6/0017* (2013.01); *A61K 6/0023* (2013.01); *A61K 6/083* (2013.01)

(58) Field of Classification Search
CPC .. A61K 6/0023; A61K 6/0029; A61K 6/0052; A61K 6/0017; A61K 6/083; C08F 220/18; C08F 2/50; C08F 30/02
USPC ......... 522/78–80; 252/182.13; 523/115–118; 433/228.1
See application file for complete search history.

(56) References Cited

U.S. PATENT DOCUMENTS

| 3,018,262 A | 1/1962 | Schroeder |
| 3,117,099 A | 1/1964 | Proops |
| 3,729,313 A | 4/1973 | Smith |

(Continued)

FOREIGN PATENT DOCUMENTS

| BE | 446 424 | 8/1942 |
| CN | 1252138 | 5/2000 |

(Continued)

OTHER PUBLICATIONS

Merck (2-hyroxypropyl methacrylate data sheet); p. 1-3.*

(Continued)

*Primary Examiner* — Michael F Pepitone
*Assistant Examiner* — Jessica M Roswell (57) ABSTRACT

The invention features a polymerizable composition that comprises a free-radically polymerizable acidic resin, and a photoinitiator system comprising a polycyclic aromatic component. The photoinitiator system may also contain a visible light sensitizer, an iodonium salt, and a tertiary amine.

23 Claims, 1 Drawing Sheet

(56) References Cited

U.S. PATENT DOCUMENTS

| | | | |
|---|---|---|---|
| 3,741,769 A | 6/1973 | Smith | |
| 3,808,006 A | 4/1974 | Smith | |
| 4,259,075 A | 3/1981 | Yamauchi et al. | |
| 4,298,738 A | 11/1981 | Lechtken et al. | |
| 4,324,744 A | 4/1982 | Lechtken et al. | |
| 4,356,296 A | 10/1982 | Griffith et al. | |
| 4,385,109 A | 5/1983 | Lechtken et al. | |
| 4,499,251 A | 2/1985 | Omura et al. | |
| 4,503,169 A | 3/1985 | Randklev | |
| 4,514,342 A * | 4/1985 | Billington et al. | 558/180 |
| 4,537,940 A | 8/1985 | Omura et al. | |
| 4,539,382 A | 9/1985 | Omura et al. | |
| 4,588,756 A | 5/1986 | Bowen et al. | |
| 4,629,746 A | 12/1986 | Schaan et al. | |
| 4,642,126 A | 2/1987 | Zador et al. | |
| 4,648,843 A | 3/1987 | Mitra | |
| 4,652,274 A | 3/1987 | Boettcher et al. | |
| 4,665,217 A | 5/1987 | Reiners et al. | |
| 4,695,251 A | 9/1987 | Randklev | |
| 4,710,523 A | 12/1987 | Lechtken et al. | |
| 4,735,632 A | 4/1988 | Oxman | |
| 4,737,593 A | 4/1988 | Ellrich et al. | |
| 4,752,338 A | 6/1988 | Reiners et al. | |
| 4,767,798 A | 8/1988 | Gasser et al. | |
| 4,828,583 A | 5/1989 | Oxman | |
| 4,835,193 A | 5/1989 | Hayase | |
| 4,872,936 A | 10/1989 | Engelbrecht | |
| 4,882,365 A | 11/1989 | Gasser | |
| 4,889,792 A | 12/1989 | Palazzotto | |
| 4,959,297 A | 9/1990 | Palazzotto | |
| 4,990,281 A * | 2/1991 | Clark | 252/184 |
| 5,026,902 A | 6/1991 | Fock et al. | |
| 5,076,844 A | 12/1991 | Fock et al. | |
| 5,130,347 A | 7/1992 | Mitra | |
| 5,154,762 A | 10/1992 | Mitra et al. | |
| 5,332,429 A | 7/1994 | Mitra | |
| 5,501,727 A | 3/1996 | Wang et al. | |
| 5,530,038 A | 6/1996 | Yamamoto et al. | |
| 5,545,676 A | 8/1996 | Palazzotto | |
| 5,624,260 A | 4/1997 | Wilcox | |
| 5,684,060 A | 11/1997 | Konings et al. | |
| 5,730,764 A | 3/1998 | Williamson | |
| 5,856,373 A | 1/1999 | Kaisaki | |
| 5,865,803 A | 2/1999 | Major | |
| 5,893,714 A | 4/1999 | Arnold | |
| 5,918,772 A | 7/1999 | Keller | |
| 5,944,419 A | 8/1999 | Streiff | |
| 5,980,253 A | 11/1999 | Oxman | |
| 5,998,495 A | 12/1999 | Oxman | |
| 5,998,499 A * | 12/1999 | Klee et al. | 523/118 |
| 6,025,406 A | 2/2000 | Oxman | |
| 6,030,606 A | 2/2000 | Holmes | |
| 6,043,295 A | 3/2000 | Oxman | |
| 6,187,833 B1 | 2/2001 | Oxman | |
| 6,251,963 B1 | 6/2001 | Kohler et al. | |
| 6,306,926 B1 | 10/2001 | Bretscher et al. | |
| 6,386,203 B1 | 5/2002 | Hammerslag | |
| 6,387,981 B1 | 5/2002 | Zhang et al. | |
| 6,458,868 B1 | 10/2002 | Okada et al. | |
| 6,572,693 B1 | 6/2003 | Wu et al. | |
| 6,703,518 B1 | 3/2004 | Xu et al. | |
| 6,730,156 B1 | 5/2004 | Windisch | |
| 6,747,071 B1 * | 6/2004 | Frances | 522/148 |
| 6,765,036 B2 | 7/2004 | Dede | |
| 6,790,877 B2 | 9/2004 | Nakatsuka et al. | |
| 6,899,948 B2 | 5/2005 | Zhang | |
| 7,026,367 B2 | 4/2006 | Kalgutkar | |
| 7,037,583 B2 | 5/2006 | Furman et al. | |
| 6,984,673 B2 | 7/2006 | Kawashima et al. | |
| 7,226,960 B2 | 6/2007 | Jin | |
| 7,247,660 B2 | 7/2007 | Frances | |
| 7,449,499 B2 | 11/2008 | Craig et al. | |
| 7,452,924 B2 | 11/2008 | Aasen et al. | |
| 2002/0156152 A1 | 10/2002 | Zhang | |
| 2003/0018098 A1 | 1/2003 | Falsafi et al. | |
| 2003/0035899 A1 | 2/2003 | Klettke | |
| 2003/0055123 A1 | 3/2003 | Kawashima et al. | |
| 2003/0166737 A1 * | 9/2003 | Dede et al. | 522/7 |
| 2003/0166740 A1 | 9/2003 | Mitra et al. | |
| 2003/0171505 A1 | 9/2003 | Bublewitz et al. | |
| 2003/0195273 A1 | 10/2003 | Mitra et al. | |
| 2004/0014009 A1 | 1/2004 | Jia et al. | |
| 2004/0057909 A1 * | 3/2004 | Moszner et al. | 424/49 |
| 2004/0110864 A1 | 6/2004 | Hecht | |
| 2004/0235981 A1 | 11/2004 | Qiaqn | |
| 2005/0070627 A1 | 3/2005 | Falsafi et al. | |
| 2005/0113477 A1 | 5/2005 | Oxman | |
| 2005/0175965 A1 | 8/2005 | Craig et al. | |
| 2005/0175966 A1 | 8/2005 | Falsafi et al. | |
| 2005/0176844 A1 | 8/2005 | Aasen et al. | |
| 2005/0252413 A1 | 11/2005 | Kangas et al. | |
| 2005/0252414 A1 | 11/2005 | Craig et al. | |
| 2005/0252415 A1 | 11/2005 | Budd et al. | |
| 2005/0256223 A1 | 11/2005 | Kolb et al. | |
| 2006/0084717 A1 | 4/2006 | Cohen et al. | |
| 2006/0144726 A1 | 7/2006 | Foust et al. | |
| 2006/0144733 A1 | 7/2006 | Wu et al. | |
| 2006/0187752 A1 | 8/2006 | Keller | |
| 2007/0090079 A1 | 4/2007 | Kelller | |
| 2007/0142497 A1 * | 6/2007 | Kalgutkar | A61K 6/0023 523/118 |
| 2007/0172789 A1 | 7/2007 | Muller | |
| 2007/0243145 A1 | 10/2007 | Andre et al. | |
| 2007/0248927 A1 | 10/2007 | Luchterhandt et al. | |
| 2008/0193759 A1 | 8/2008 | Rieger et al. | |
| 2008/0293846 A1 | 11/2008 | Craig et al. | |
| 2008/0306168 A1 | 12/2008 | Craig et al. | |
| 2009/0005469 A1 | 1/2009 | Craig | |
| 2009/0047486 A1 | 2/2009 | Jones et al. | |
| 2009/0075239 A1 | 3/2009 | Abuelyaman | |

FOREIGN PATENT DOCUMENTS

| | | |
|---|---|---|
| EP | 0 173 567 | 3/1986 |
| EP | 173567 | 3/1986 |
| EP | 0 189 540 | 8/1986 |
| EP | 189540 | 8/1986 |
| EP | 0 201 031 | 11/1986 |
| EP | 0 201 778 | 11/1986 |
| EP | 0 238 025 | 9/1987 |
| EP | 285369 | 10/1988 |
| EP | 320127 | 6/1989 |
| EP | 0 373 384 | 6/1990 |
| EP | 412430 | 2/1991 |
| EP | 0 712 622 | 5/1996 |
| EP | 728970 | 8/1996 |
| EP | 1 051 961 | 11/2000 |
| EP | 1340472 | 9/2003 |
| EP | 1465579 | 10/2004 |
| EP | 1586294 | 10/2005 |
| JP | 63273602 | 11/1988 |
| JP | 10147608 | 6/1998 |
| JP | 11322944 | 11/1999 |
| JP | 2001520758 | 10/2001 |
| WO | WO 1995014716 | 6/1995 |
| WO | WO 1998022521 | 5/1998 |
| WO | WO 1998047046 | 10/1998 |
| WO | WO 1998047047 | 10/1998 |
| WO | WO 1999027892 | 6/1999 |
| WO | WO 2000019966 | 4/2000 |
| WO | WO 2000019967 | 4/2000 |
| WO | WO 00/38619 | 7/2000 |
| WO | WO 00/42092 | 7/2000 |
| WO | WO 01/07444 | 2/2001 |
| WO | WO 01/30305 | 5/2001 |
| WO | WO 2001051540 | 7/2001 |
| WO | WO 01/92271 | 12/2001 |
| WO | WO 03/063804 | 8/2003 |
| WO | WO 2005051332 | 6/2005 |
| WO | WO 2006/055328 | 5/2006 |
| WO | WO 2006098882 | 9/2006 |
| WO | WO 2007079144 | 7/2007 |

(56) References Cited

FOREIGN PATENT DOCUMENTS

| WO | WO 2007079166 | 7/2007 |
|---|---|---|
| WO | WO 2009152211 | 12/2009 |

OTHER PUBLICATIONS

Komura et al., machine English translation of JP 58-021607 (abstract only); Jul. 1981.*
N.L. Weinburg, Ed., Technique of Electroorganic Synthesis Part II Techniques of Chemistry, vol. V (1975).
C.K. Mann and K.K. Barnes, Electrochemical Reactions in Nonaqueous Systems, 1970.
Moszner et al., "Chemical aspects of self-etching enamel-dentin adhesives: A systematic review," Dental Materials, 2005; 21:895-910.
Salz et al., "Adhesive Performance of New Hydrolytically Stable One-component Self-etching Enamel/Dentin Adhesives," The Journal of Achesive Dentistry, 2010; 12(1):7-11.
Written Opinion of the International Searching Authority for International Application No. US2006/049427, 4 pages.
Written Opinion of the International Searching Authority for International Application No. US2006/049463, 4 pages.
Beringer, Diarylidonium Salts, IX, The Synthesis of Substituted Diphenyliodonium Salts, J. Am. Chem. Soc., vol. 81, pp. 342-351, (1959).
Constantine, Biphenylenes, Part XIV, Synthesis of 1- and 2-Phenyl-, 2,7-Dimethyl- and 2,3,6,7-Tetramethyl-Biphenylene, J. Chem. Soc. (C), vol. 19, pp. 1767-1769, (1966).
DIN EN ISO 4049, "Dentistry—Polymer-Based Filling, Restorative and Luting Meterials", Jan. 2001, pp. 1-29.
"Hydroxypropl Methacrylate (Stabilised)", Merck KGaA, Darmstadt, Germany, [online], retrieved from the internet on Jul. 14, 2010, <www.merck-chemicals.com/hydroproply-methacrylate/MDA_CHEM-800610/p_ . . . >, pp. 1-3.
ISO 9917-1, "Dentistry—Water-Based Cements—Part 1: Powder/Liquid Acid-Base Cements", Nov. 1, 2003, pp. 1-22.
Lee, Handbook of Epoxy Resins, McGraw-Hill Inc., (1967).
Wilcox, Jr., Preparation of Alykl-Substituted Biphenylenes by the Pyrolytic Extrusion of Nitrogen From Benzo[C]Cinnolines, J. Org. Chem. vol. 53, pp. 4333-4339, (1988).
Intl Preliminary Report on Patentability and Written Opinion for PCT/US2006/049249, 5 pages.
Intl Search Report for PCT/US2006/049249, 3 pages.
Intl Search Report for PCT/US2006/049427, 3 pages.
Intl Search Report for PCT/US2006/049463, 3 pages.
Intl Search Report for PCT/US2003/000522, 2 pages.
Written Opinion for PCT/US2003/000522, 5 pages.
Intl Preliminary Report on Patentability and Written Opinion for PCT/US2009/046850, 5 pages.
Intl Search Report for PCT/US2009/046850, 2 pages.

* cited by examiner

*Fig. 1*

*Fig. 2*

DENTAL COMPOSITIONS AND INITIATOR SYSTEMS WITH POLYCYCLIC AROMATIC COMPONENT

CROSS REFERENCE TO RELATED APPLICATIONS

This application is a national stage filing under 35 U.S.C. 371 of PCT/US2006/049249, filed Dec. 22, 2006, which claims benefit to U.S. Provisional Application No. 60/754,952, filed Dec. 29, 2005 the disclosure of which is incorporated by reference in its entirety herein.

FIELD OF THE INVENTION

This invention relates to photoinitiator systems for curing polymerizable monomers. More specifically, this invention relates to polymerizable dental compositions that contain a free-radically polymerizable acidic component and a photoinitiator system comprising a polycyclic aromatic component that is activated upon exposure to visible light.

BACKGROUND

The restoration of teeth commonly involves the use of (meth)acrylate-based free-radically polymerizable resins that can be chemically cured or light cured. Chemical curing typically involves a redox system with a peroxide oxidizing agent and an amine reducing agent that produces free radicals that initiate polymerization. Light curing typically involves a photoinitiator system that produces free radicals upon exposure to light.

Certain photoinitiator systems that have been introduced for use in dental restorative compositions include systems that produce free radicals via visible light (400-1000 nm). Photoinitiator systems also have been used in conjunction with cationically curing dental compositions, for example epoxy-based resins, by way of a cationic ring-opening polymerization curing mechanism. For example, ternary photoinitiator systems comprising an iodonium salt, a visible light absorber, and an electron donor have been utilized for curing both free-radically cured (meth)acrylate resins and cationically cured epoxy resins. Additionally, polycyclic aromatics have also been described for use as electron donors in cationically curing epoxy resin systems. Although these systems represent an improvement on older systems, they can sometimes experience sluggish or incomplete cure under certain conditions. Consequently, a need remains for polymerizable dental compositions (e.g., dental adhesives) with better curing performance than conventional systems, while still exhibiting satisfactory bond strengths.

SUMMARY

The present invention is directed to new polymerizable compositions, for example compositions that fulfill the need for satisfactory cure and bond performance in dental adhesive systems. In one embodiment, the composition includes (a) a polymerizable acidic component, and (b) a photoinitiator system comprising a polycyclic aromatic component. The acidic component is typically a free-radically polymerizable component, such as a phosphorylated (meth)acrylate monomer system. The polycyclic aromatic component may be, for example, an anthracene derivative, a biphenylene derivative, or combinations thereof.

In some embodiments, the anthracene derivative is unsubstituted anthracene, or anthracene substituted by organic groups including an alkyl, aryl (e.g., phenyl), aryloxy, alkoxy, or combinations thereof. The alkyl substituted anthracene may be, for example, 2,6-di-tert-butylanthracene, 9-methylanthracene, or 9,10-dimethylanthracene. The alkoxy substituted anthracene may be, for example, 2-ethyl-9,10-dimethoxyanthracene (EDMOA), 9,10-diethoxyanthracene, 1,4-dimethoxyanthracene, or 9,10-dimethoxyanthracene. In other embodiments, the biphenylene derivative is unsubstituted biphenylene.

In certain embodiments, the photoinitiator system comprises a polycyclic aromatic component and a tertiary amine, wherein the tertiary amine may be, for example, ethyl-4-dimethylamino benzoate (EDMAB). The photoinitiator system may further comprise a visible light sensitizer, for example camphorquinone. Typically, the photopolymerizable composition further comprises an iodonium salt, for example diphenyliodonium hexafluorophosphate.

By using a polycyclic aromatic component in the photoinitiator system, the present invention achieves desirable cure and bond strength performance. A typical photoinitiator system comprises EDMOA, EDMAB, a visible light sensitizer such as camphorquinone, and preferably an iodonium salt. In general, the dual donor system of EDMOA and EDMAB shows enhanced cure and bond strength compared to photoinitiator systems containing either a polycyclic aromatic compound or a tertiary amine alone. This suggests that the polycyclic aromatic component acts synergistically with the tertiary amine.

In some embodiments of the present invention, dental adhesive compositions will possess enhanced curing rates and bond strengths as compared to previous dental adhesives. The increased rate of curing will decrease the amount of time the patient needs to spend in the dentist's office.

By "polycyclic aromatic component" is meant a polycyclic organic compound having two or more fused aromatic rings, including their alkyl-, alkoxy-, aryl-, and aryloxy-substituted derivatives. By "fused" is meant two aromatic rings with a shared side or with opposing sides directly joined by carbon-carbon bonds.

By "polymerizable acidic component" or "polymerizable free-radically acidic component" is meant an acidic monomer that can be free-radically polymerized (ie, cured or hardened) in the presence of free radicals generated from a photo and/or a redox initiator system.

The recitation herein of numerical ranges by endpoints is intended to include all numbers subsumed within that range (e.g. 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The above summary is not intended to describe each embodiment or every implementation of the invention. Other embodiments, features, and advantages of the present invention will be apparent from the following detailed description thereof, and from the claims.

DETAILED DESCRIPTION

The invention provides a polymerizable composition that comprises a free-radically polymerizable acidic component and a photoinitiator system that contains a polycyclic aromatic component. Additionally, the photoinitiator system may contain an iodonium salt, a visible light absorber, and an amine electron donor, e.g. a tertiary amine. The compositions of the invention typically are dental compositions, e.g., dental adhesives, and include an anthracene derivative, a biphenylene derivative, or combinations thereof as the polycyclic aromatic component.

In some embodiments, the invention provides a photoinitiator system that comprises an amine electron donor, a polycyclic aromatic component, an optional iodonium salt, and an optional visible light absorber. Such initiators can be included in polymerizable dental compositions, e.g., dental adhesives, that include a free-radically polymerizable component, for example an acidic component. The combination of the polycyclic aromatic component and the amine electron donor as part of the photoinitiator system can provide improved curing rates and/or increased bond strengths.

Advantageously, the photopolymerizable compositions of the invention are sensitive throughout the "visible light" region and polymerize without appreciable application of heat. The term "visible light" is used throughout this application to refer to light having a wavelength of about 400 to 1000 nanometers (nm). Photopolymerization of the compositions takes place upon exposure of the compositions to a source of actinic radiation having a wavelength within this spectral region.

Polymerizable Component

Suitable polymerizable components that can be used in dental materials and dental adhesive compositions in the methods of the present invention include ethylenically unsaturated compounds (which contain free radically active unsaturated groups, e.g., acrylates and methacrylates) and combinations thereof. In one embodiment, the polymerizable component comprises a phosphorylated monomer, such as a phosphorylated (meth)acrylate.

Ethylenically Unsaturated Compounds with Acid Functionality

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl)phosphate, bis((meth)acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable resin system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain embodiments of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Provisional Application Ser. No. 60/600,658 (entitled "SELF-ADHESIVE COMPOSITIONS INCLUDING A PLURALITY OF ACIDIC COMPOUNDS"), filed on Aug. 11, 2004.

Typically, the compositions of the present invention include at least 1% by weight, more typically at least 3% by weight, and most typically at least 5% by weight ethylenically unsaturated compounds with acid functionality, based on the total weight of the unfilled composition. Typically, compositions of the present invention include at most 80% by weight, more typically at most 70% by weight, and most typically at most 60% by weight ethylenically unsaturated compounds with acid functionality, based on the total weight of the unfilled composition.

Ethylenically Unsaturated Compounds without Acid Functionality

The compositions of the present invention may also include one or more polymerizable components in addition to the ethylenically unsaturated compounds with acid functionality, thereby forming hardenable compositions. The additional polymerizable components may be monomers, oligomers, or polymers.

In certain embodiments, the compositions are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Typically, compositions of the present invention include at least 5% by weight, more typically at least 10% by weight, and most typically at least 15% by weight ethylenically unsaturated compounds without acid functionality, based on the total weight of the unfilled composition. Typically, compositions of the present invention include at most 95% by weight, more typically at most 90% by weight, and most typically at most 80% by weight ethylenically unsaturated compounds without acid functionality, based on the total weight of the unfilled composition.

Photopolymerizable Compositions

Suitable photopolymerizable compositions may include photopolymerizable components (e.g., compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis [1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth) acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth) acrylates as disclosed, for example, in U.S. Pat. No. 5,076, 844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

Suitable photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones, diketones, and alpha diketones that absorb some light within a range of 400 nm to 520 nm (preferably, 450 nm to 500 nm). Typical compounds include camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. Publication No. 2003/0166737 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl)phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Chemically Polymerizable Compositions

The chemically polymerizable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Typically, the reducing agent is present in an amount of at least 0.01% by weight, and more typically at least 0.1% by weight, based on the total weight (including water) of the components of the polymerizable composition. Typically, the reducing agent is present in an amount of no greater than 10% by weight, and more typically no greater than 5% by weight, based on the total weight (including water) of the components of the polymerizable composition.

Typically, the oxidizing agent is present in an amount of at least 0.01% by weight, and more preferably at least 0.10% by weight, based on the total weight (including water) of the components of the polymerizable composition. Typically, the oxidizing agent is present in an amount of no greater than 10% by weight, and more typically no greater than 5% by weight, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

Polycyclic Aromatic Component

In some embodiments of the invention, a free-radically polymerizable component is combined with a photoinitiator system, wherein the photoinitiator system includes a polycyclic aromatic component and an amine electron donor. In other embodiments, a free-radically polymerizable acidic component is combined with a photoinitiator system, wherein one component of the initiator system is a polycyclic aromatic component. One class of polycyclic aromatic component compounds useful in photoinitiator systems according to the invention comprises polycyclic aromatic compounds (i.e., polycyclic compounds having two or more fused or joined aromatic rings), including their alkyl- and aryl-substituted derivatives. By "fused" is meant two aromatic rings with a shared side or with opposing sides directly joined by carbon-carbon bonds.

Representative classes of useful polycyclic aromatic compounds include, but are not limited to, biphenylenes, naphthalenes, anthracenes, benzanthracenes, pyrenes, azulenes, pentacenes, decacyclenes, and derivatives (such as acenaphthenes) and combinations thereof. Typically useful polycyclic aromatic compounds include 1,4-dimethoxyanthracene, 9-methylanthracene, 9,10-methylanthracene, anthracene, biphenylene, and combinations thereof.

More specifically, polycyclic aromatic compounds conforming to the structures shown below may be employed.

In the foregoing structures, the substituents $R_1$ to $R_{14}$ may be any group that does not have a substantially adverse effect on polymerization, and preferably are independently selected from H or hydrocarbon groups. The hydrocarbon groups may be alkyl groups (e.g., $C_{1-10}$ alkyl, $C_{2-10}$ alkenyl, or $C_{3-10}$ cycloalkyl groups) or aromatic groups (e.g., $C_{5-10}$ aromatic groups). The hydrocarbon groups can be optionally substituted by one or more halogen, —CN, —OH, —SH, —COOH, —COOC$_{1-10}$ alkyl, —(C$_{1-10}$ alkyl)$_{0-1}$-COH, —(C$_{1-10}$ alkyl)$_{0-1}$-CO—C$_{1-10}$ alkyl, —CO—C$_{1-10}$ alkyl, as well as other hydrocarbon groups. The various R-group substituents may also cooperate to form an aromatic or cycloalkyl ring. Typical R-group substituents are methyl, ethyl, methoxy, and ethoxy.

Suitable polycyclic aromatic electron donor compounds include: biphenylene, anthracene, 9-methylanthracene, 9-vinyl anthracene, 9-phenylanthracene, 9,10-diphenylanthracene, 9,10-dimethylanthracene, 2-ethylanthracene, acenaphthene, pyrene, pentacene, decacyclene, azulene, 7,12-dimethyl-1,2-benzanthracene, 1,2-benzanthracene, 1,4-dimethylnaphthalene, 2,3,5-trimethylnaphthalene, and combinations thereof. All of these compounds are available from Sigma-Aldrich, St. Louis, Mo.

Suitable polycyclic aromatic compounds include anthracene derivatives. More specifically, anthracene-based electron donor compounds conforming to the structure I shown below may be employed.

I

In the above structure I, the substituents R$_1$ to R$_{10}$ may be any group that does not have a substantially adverse effect on acidic polymerization, and are independently selected from H, alkyl groups, aryl groups and/or alkoxy groups, preferably C$_1$-C$_{10}$ alkyl and/or C$_1$-C$_{10}$ alkoxy. Typical R-group substituents are methyl, ethyl, propyl, butyl, tert-butyl, methoxy, and ethoxy.

Particularly useful anthracene-based compounds include: 2-ethyl-9,10-dimethoxyanthracene (EDMOA), 9,10-dimethylanthracene, 9,10-diethoxyanthracene, 1,4-dimethoxyanthracene, 9-methylanthracene, 2-ethylanthracene, 2-tert-butylanthracene, 2,6-di-tert-butylanthracene, 9,10-diphenyl-2,6-di-tert-butylanthracene, and combinations thereof. All of these compounds with the exception of the 2,6-di-tert-butylanthracene derivatives are available from Sigma-Aldrich, St. Louis, Mo. The anthracene-based compounds for use in the invention may possess one or more (and more preferably several if not all) of the following properties: (a) they are soluble or partially soluble in the polymerizable composition; (b) they do not absorb a significant amount of light at the wavelength of the light used to photopolymerize the composition, typically the wavelength at which the visible light sensitizer exhibits maximum absorption, by which it is meant that the polycyclic aromatic compound does not detrimentally affect the performance of the visible light sensitizer; (c) they have an oxidation potential (E$_{ox}$) greater than 0 but less than that of 1,4-dimethoxybenzene when measured versus a saturated calomel electrode (SCE); (d) a pk$_b$ greater than about 8; (e) they impart not more than a minimal amount of objectionable color to the photopolymerized component; and (f) they cause no more than a minimal amount of polymerization inhibition. Other factors that may influence the selection of the anthracene-based compound for a particular composition include the polymerizable component, the iodonium salt, and the visible light sensitizer that have been chosen, as well as the shelf stability of the polymerizable composition.

While suitable anthracene-based compounds for use in the invention have an E$_{ox}$ greater than zero and less than or equal to that of 1,4-dimethoxybenzene, it is more suitable that the anthracene-based compound have an E$_{ox}$ that is less than about 1.35 volts when measured using a saturated calomel electrode (SCE), and even more suitable that the E$_{ox}$ be between about 0.5 and 1.34 volts (vs. a SCE). E$_{ox}$ values can be measured experimentally, or obtained from established reference sources, such as N. L. Weinburg, Ed., *Technique of Electroorganic Synthesis Part II Techniques of Chemistry*, Vol. V (1975), and C. K. Mann and K. K. Barnes, *Electrochemical Reactions in Nonaqueous Systems* (1970).

Advantageously, the anthracene-based compound may accelerate the rate of polymerization (as measured by gel time) of the polymerizable resin, as compared to compositions without the electron donor compound. For many uses of the photopolymerizable compositions, the gel time is preferably less than 60 minutes, more preferably less than about 10 minutes, and most preferably less than about 2 minutes as established according to the gel time protocol as reported in U.S. Pat. Application No. 2003/0166737 (Dede et al.).

Additionally, as described herein, the photoinitiator system may contain an iodonium salt, e.g., a diaryliodonium salt. The iodonium salt should be soluble in the composition and preferably is shelf-stable, meaning it does not spontaneously promote polymerization when dissolved therein in the presence of the visible light sensitizer and the electron donor compound. Accordingly, selection of a particular iodonium salt may depend to some extent upon the particular resin, visible light sensitizer and electron donor that are chosen.

Another component in the photoinitiator system may be a visible light sensitizer, as described above The visible light sensitizer should be partly or fully soluble in the photopolymerizable composition, free of functionalities that would substantially interfere with the polymerization process, and capable of light absorption somewhere within the range of wavelengths between about 400 and about 1000 nanometers. Suitable visible light sensitizers contain one or more carbonyl functional groups. An especially suitable light sensitizer is camphorquinone.

As described above, the photoinitiator system may also contain an amine electron donor, typically a tertiary amine, as described herein. An especially suitable tertiary amine is ethyl-4-dimethylamino benzoate.

The individual components of the photoinitiator system are provided in photopolymerizingly effective amounts (i.e., amounts effective to yield a photoinitiator system that can initiate photopolymerization of the polymerizable component or, more preferably, that can accelerate the rate of polymerization). Preferably, the visible light sensitizer is present at about 0.05-5.0 weight percent based on the overall photopolymerizable composition, more preferably, at about 0.10-2.0 weight percent. The iodonium salt is preferably present at about 0.05-10.0 weight percent, more preferably at about 0.20-5.0 weight percent, and most preferably at about 0.40-3.0 weight percent, based on the overall composition. The amine electron donors are preferably present at about 0.01-5.0 weight percent, more preferably about 0.05-2.0 weight percent, and most preferably about 0.05-1.0 weight percent, based on the overall composition.

The polycyclic aromatic compound or compounds (e.g. an anthracene derivative or a biphenylene) are preferably present at about 0.01-5.0 weight percent, more preferably about 0.05-1.0 weight percent, and most preferably about 0.05-0.50 weight percent, based on the overall composition.

Fillers

The compositions of the present invention can optionally contain one or more additional fillers. Fillers may be selected from one or more of a wide variety of materials suitable for incorporation in compositions used for dental applications, such as fillers currently used in dental restorative compositions, and the like. Particularly useful fillers are described in U.S. Patent Application No. 60/754,985, filed Dec. 29, 2005.

The choice of the filler affects important properties of the dental composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Acidically polymerizable compositions of the invention can be prepared with refractive indices which approach or approximate the refractive indices of fillers such as quartz (refractive index 1.55), submicron silica (refractive index 1.46), and 5.5:1 mole ratio SiO:ZrO, non-vitreous microparticles (refractive index 1.54). In this way, the appearance of the dental material can, if desired, be made to closely approximate the appearance of natural dentition.

Radiopacity is a measurement of the ability of the dental composite to be detected by x-ray examination. Frequently a radiopaque dental composite will be desirable, for instance, to enable the dentist to determine whether or not a dental restoration remains sound. Under other circumstances a non-radiopaque composite may be desirable. Suitable fillers for radiopaque formulations are described in EP-A2-0 189 540, EP-B-0 238 025, and U.S. Pat. No. 6,306,926 B1.

The amount of filler which is incorporated into the composite, referred to herein as the "loading level" and expressed as a weight percent based on the total weight of the dental material, will vary depending on the type of filler, the curable resin and other components of the composition, and the end use of the composite.

For some dental materials, such as sealants, the acidic polymerizable compositions of the invention can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 60 and 90 weight percent is generally preferred.

The filler(s) used in the compositions of the invention is preferably finely divided. The filler(s) can have a unimodal or polymodial (e.g., bimodal) particle size distribution. Typically, the maximum particle size (the largest dimension of a particle, generally, the diameter) of the filler(s) is less than 20 micrometers, more typically less than 10 micrometers, and most preferably less than 5 micrometers. Typically, the average particle size of the filler(s) is less than 0.1 micrometers, and more typically less than 0.075 micrometer.

The compositions may include a filer comprising an inorganic material. It can also be a crosslinked organic material that is insoluble in the resin system, and is optionally filled with inorganic filler. The filler(s) should in any event be nontoxic and suitable for use in the mouth. The filler(s) can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles include quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially useful in certain embodiments.

Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

The composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Other suitable fillers are disclosed in U.S. Pat. No. 6,387,981 (Zhang et al.); U.S. Pat. No. 6,572,693 (Wu et al.); U.S. Pat. No. 6,730,156 (Windisch); and U.S. Pat. No. 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

For some embodiments of the present invention that include filler (e.g., dental adhesive compositions), the compositions typically include at least 1% by weight, more typically at least 2% by weight, and most typically at least 5% by weight filler, based on the total weight of the composition. For such embodiments, compositions of the present invention typically include at most 40% by weight, more typically at most 20% by weight, and most typically at most 15% by weight filler, based on the total weight of the composition.

For other embodiments (e.g., wherein the composition is a dental restorative or an orthodontic adhesive), compositions of the present invention typically include at least 40% by weight, more typically at least 45% by weight, and most typically at least 50% by weight filler, based on the total weight of the composition. For such embodiments, compositions of the present invention typically include at most 90% by weight, more typically at most 80% by weight, even more typically at most 70% by weight filler, and most typically at most 50% by weight filler, based on the total weight of the composition.

Other Additives

Optionally, compositions of the present invention may contain solvents (e.g., alcohols (e.g., propanol, ethanol), ketones (e.g., acetone, methyl ethyl ketone), esters (e.g., ethyl acetate), and/or other nonaqueous solvents (e.g., dimethylformamide, dimethylacetamide, dimethylsulfoxide, 1-methyl-2-pyrrolidinone)). In some embodiments, the composition may contain a water scavenger, as is described in U.S. Patent Application No. 60/754,953, filed Dec. 29, 2005.

If desired, the compositions of the invention can contain additives such as indicators, dyes (including photobleachable dyes), pigments, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

The amounts and types of each ingredient in the dental material should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on previous experience with dental materials. When the dental material is applied to a tooth, the tooth can optionally be pre-treated with a primer and/or an adhesive by methods known to those skilled in the art.

Preparation and Use of the Compositions

The dental compositions of the present invention can be prepared by combining all the various components using conventional mixing techniques. Typically, photopolymerizable compositions of the invention are prepared by simply admixing, under "safe light" conditions, the components of the inventive compositions. Suitable inert solvents may be employed if desired when affecting this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the polymerizable resin, with or without the use of mild heating to facilitate dissolution.

The compositions can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation.

The components of the composition can be included in a kit, where the contents of the composition are packaged to allow for storage of the components until they are needed.

The components of the composition can be mixed and clinically applied using conventional techniques. A curing light is generally required for the initiation of photopolymerizable compositions.

The compositions of the invention are particularly well adapted for use as a wide variety of dental materials, which may be filled or unfilled. Exemplary dental materials include dental restoratives (e.g., composites, fillings, sealants, inlays, onlays, crowns, and bridges), orthodontic appliances, and orthodontic adhesives. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

The initiator systems of the invention are particularly effective for use in non-aqueous compositions used to etch, preferably etch and prime, at least one type of dental structure (e.g., dentin, enamel, or bone). These compositions can be used with an overlying adhesive (e.g., a dental adhesive), but they more preferably can be used as the adhesive (i.e., a self-etching adhesive). In some implementations, the compositions can be in the form of a self-adhesive dental restorative or orthodontic adhesive.

Self-etching adhesives according to the invention may be applied to a dental structure using any suitable method, including any of the following:

A first method is for the practitioner to leave the structure surface wet with water after rinsing, and therefore, eliminate or partially eliminate a typical drying step before structure treatment. A non-aqueous, self-etching dental composition (e.g., a self-etching adhesive, a self-adhesive composition, or an orthodontic adhesive) can than be applied to the structure surface and cured using conventional methods.

A second method ("wet-brush" technique) is to sequentially dip a dental applicator into an aqueous diluent (e.g. water or water plus one or more additives), and then mix the wet brush with a non-aqueous, self-etching dental composition (e.g., a self-etching adhesive). The resulting aqueous mixture can than be applied to the structure surface and cured using conventional methods.

A third method is to sequentially treat a dry dental structure surface with an aqueous diluent (e.g. water or water plus one or more additives), followed by the application of a non-aqueous, self-etching dental composition (e.g., a self-etching adhesive, a self-adhesive composition, or an orthodontic adhesive). The resulting treated surface can then be further treated and cured using conventional methods.

In some embodiments of the present invention, conditions effective to cause a composition (preferably, adhesive) to etch a dental structure surface include swishing the adhesive and/or adhesive/diluent mixture with a brush to mix/rubbing dental structure surface for a time effective to etch (i.e., for at least 3 seconds), typically for at least 5 seconds, often times for at least 10 seconds, and sometimes for at least 20 seconds.

Methods of bonding a dental material to a dental structure surface preferably result in a bond to enamel or dentin (or preferably both), of at least 7 MPa, more preferably at least 15, MPa, and most preferably at least 20 MPa.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Notched Edge Shear Adhesive Test Method (Uncut Enamel, Cut Enamel, or Dentin)

Adhesive shear bond strength to uncut enamel for a given test sample was evaluated by the following procedure. Modifications of the procedure for cut enamel and dentin are indicated.

Preparation of Test Teeth.

Bovine incisal teeth were obtained from a local slaughterhouse, the roots cut off, and the pulp removed. The teeth, free of soft tissue, were embedded in circular acrylic disks so that the labial surfaces of the teeth were exposed. The embedded teeth were stored in deionized water in a refrigerator prior to use.

Preparation of Adhesion Test Samples.

The exposed labial surfaces of the embedded teeth were prophied using a prophy paste in order to clean the tooth surfaces prior to bonding.

For testing on cut enamel or dentin, the embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process.

An adhesive test sample was applied with a dental applicator brush over the exposed labial tooth surface and light cured for 10 seconds with an XL 3000 dental curing light (3M Company, St. Paul, Minn.). A 2-mm thick Teflon mold with a hole approximately 2.38 mm in diameter was clamped to the embedded tooth such that the hole in the mold exposed the flattest available area of the adhesively prepared tooth surface. A composite material, FILTEK Z250 Universal Restorative (3M Company), was filled into the hole such that the hole was completely filled, but not overfilled, and light cured per manufacturer's directions to form a "button" that was adhesively attached to the tooth. For testing on cut enamel or dentin, two "buttons" were adhesively attached to the tooth.

The finished test samples were stored in deionized water at 37° C. for approximately 24 hours prior to testing.

Sample Testing.

The molds were carefully removed from the embedded teeth, leaving the buttons attached to the tooth surfaces. One at a time the test samples were mounted in a holder clamped in the jaws of an Instron™ (Instron 4505, Instron Corp. Canton, Mass.) with the tooth surface oriented parallel to the direction of the pushing shear force. A metal fixture with a semicircular notched edge was attached to the Instron, and the notched edge was carefully fitted onto the button, flush with the tooth surface. The pushing shear force was started at a crosshead speed of 1 mm/min. The force in kilograms (kg) at which the bond failed was recorded, and this number was converted to a force per unit area (units of $kg/cm^2$ or MPa) using the known surface area of the button. Each reported value of adhesion to enamel or adhesion to dentin represents the average of 2 to 10 replicates.

Wire-Loop Shear Adhesive Test Method (Cut Enamel or Dentin)

Adhesive shear bond strength to cut enamel or dentin for a given test sample was evaluated by the following procedure Preparation of Test Teeth.

Bovine incisal teeth were obtained from a local slaughterhouse, the roots cut off, and the pulp removed. The teeth, free of soft tissue, were embedded in circular acrylic disks. The embedded teeth were stored in deionized water in a refrigerator prior to use.

Preparation of Adhesion Test Samples.

The embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process.

An adhesive test sample was applied with a dental applicator brush over the flat enamel or dentin surface of the prepared surface and light cured for 10 seconds with an XL 3000 dental curing light (3M Company). A 2.5-mm thick Teflon mold with a hole approximately 4.7 mm in diameter was clamped to the embedded tooth such that the hole in the mold exposed part of the adhesively prepared tooth surface. A composite material, FILTEK Z250 Universal Restorative (3M Company), was filled into the hole such that the hole was completely filled, but not overfilled, and light cured per manufacturer's directions to form a "button" that was adhesively attached to the tooth.

The finished test samples were stored in deionized water at 37° C. for approximately 24 hours prior to testing. The holes in the Teflon molds were lined with thin gelatin capsules that dissolved when stored in water, thus making it easier to remove the molds from the buttons.

Sample Testing.

The molds were carefully removed from the embedded teeth, leaving the buttons attached to the tooth surfaces. One at a time the test samples were mounted in a holder clamped in the jaws of an Instron 4505 machine (Instron Corp. Canton, Mass.) with the tooth surface oriented parallel to the direction of the pulling shear force. A loop of orthodontic wire (0.75-mm diameter) was placed around the button flush to the polished tooth surface, and the pulling shear force was started at a crosshead speed of 2 mm/min. The force in kilograms (kg) at which the bond failed was recorded, and this number was converted to a force per unit area (units of $kg/cm^2$ or MPa) using the known surface area of the button. Each reported value of adhesion to enamel or adhesion to dentin represents the average of 2 to 10 replicates.

Abbreviations, Descriptions, and Sources of Materials

| Abbreviation | Description and Source of Material |
|---|---|
| TEGDMA | Triethyleneglycol dimethacrylate (Sartomer, Exton, PA) |
| UDMA | Diurethane dimethacrylate (CAS No. 41137-60-4), commercially available as Rohamere 6661-0 (Rohm Tech, Inc., Malden, MA) |
| PEG 400 DMA | Polyethyleneglycol dimethacrylate (MW about 570; Sartomer) |
| TMP TMA | Trimethylolpropane trimethacrylate (Sigma-Aldrich, St. Louis MO) |
| MHP | Methacryloyloxyhexyl phosphate ($P_2O_5$ derived) (See Preparation Method described herein) |
| HEMA-P | Mixture of mono-, di-, tri-HEMA phosphate and tetraHEMA pyrophosphate. (See Preparation Method described herein) |
| EDMAB | Ethyl 4-(N,N-dimethylamino)benzoate (Sigma-Aldrich) |
| DPIHFP | Diphenyliodonium hexafluorophosphate (Johnson Matthey, Alpha Aesar Division, Ward Hill, NJ) |
| CPQ | Camphorquinone (Sigma-Aldrich) |
| EDMOA | 2-Ethyl-9,10-dimethoxyanthracene (Sigma-Aldrich) |
| Zirconia Sol | Zirconia sol having 44.53% solids, 40.41% zirconia; prepared as described for Preparation Example 3 in U.S. Patent Application No. 11/078468, filed Mar. 14, 2005 and entitled "Light Management Films with Zirconia Particles" |
| AMBERLITE IR-120(Plus) | Ion-exchange resin; strongly acidic gel-type resin useful in catalytic applications (Sigma-Aldrich) |
| SPMA K-Salt | 3-Sulfopropyl methacrylate, potassium salt (Sigma-Aldrich) |

Starting Materials Preparations

6-Methacryloxyhexyl Phosphate (MHP from $P_2O_5$)

6-Hydroxyhexyl Methacrylate Synthesis: 1,6-Hexanediol (1000.00 g, 8.46 mol, Sigma-Aldrich) was placed in a 1-liter 3-neck flask equipped with a mechanical stirrer and a narrow tube blowing dry air into the flask. The solid diol was heated to 90° C., at which temperature all the solid melted. With continuous stirring, p-toluenesulfonic acid crystals (18.95 g, 0.11 mol) followed by BHT (2.42 g, 0.011 mol) and methacrylic acid (728.49.02 g, 8.46 mol). Heating at 90° C. with stirring was continued for 5 hours during which time vacuum was applied using tap water aspirator for 5-10 minutes after each half-hour reaction time. The heat was turned off and the reaction mixture was cooled to room temperature. The viscous liquid obtained was washed with 10% aqueous sodium carbonate twice (2×240 ml), followed by washing with water (2×240 ml), and finally with 100 ml of saturated NaCl aqueous solution. The obtained oil was dried using anhydrous $Na_2SO_4$ then isolated by vacuum filtration to give 1067 g (67.70%) of 6-hydroxyhexyl methacrylate, a yellow oil. This desired product was formed along with 15-18% of 1,6-bis(methacryloyloxyhexane). Chemical characterization was by NMR analysis.

6-Methacryloxyhexyl Phosphate Synthesis: A slurry was formed by mixing $P_4O_{10}$ (178.66 g, 0.63 mol) and methylene chloride (500 ml) in a 1-liter flask equipped with a mechanical stirrer under $N_2$ atmosphere. The flask was cooled in an ice bath (0-5° C.) for 15 minutes. With continuous stirring, 6-hydroxyhexyl methacrylate (962.82 g, which contained 3.78 mol of the mono-methacrylate, along with its dimethacrylate by-product as described above) was added to the flask slowly over 2 hours. After complete addition, the mixture was stirred in the ice bath for 1 hour then at room temperature for 2 hours. BHT (500 mg) was added, and then the temperature was raised to reflux (40-41° C.) for 45 minutes. The heat was turned off and the mixture was allowed to cool to room temperature. The solvent was removed under vacuum to afford 1085 g (95.5%) of 6-Methacryloxyhexyl Phosphate as a yellow oil. Chemical characterization was by NMR analysis.

HEMA-P (Mixture of HEMA Phosphates and tetraHEMA Pyrophosphate)

A 1-liter three-necked round-bottomed flask fitted with a reflux condenser with gas inlet, a mechanical stirrer, and an addition funnel with gas outlet was charged with 76.7 g of $POCl_3$ and 500 ml THF. A solution of 130.5 g HEMA, 101.5 g triethylamine (TMA) and 87 g of THF was placed in the addition funnel. The flask was cooled via an ice-water-salt bath to approximately −5° C. The solution was added dropwise with stirring over a period of 25 minutes during which the temperature was maintained between 0° C. and −5° C. The mixture was stirred for three hours allowing the temperature to rise to room temperature. To the flask was added an additional 200 ml of THF to facilitate stirring. To the addition funnel was added a solution of 51 g of TEA and 6.8 g water in 50 ml of THF. After cooling the flask to 0-5° C. via the ice-water-salt bath, the solution was added dropwise during 16 minutes. The mixture was allowed to come to room temperature and stirred for 18 hours. The mixture was filtered to remove the precipitated salts and the THF removed in vaccuo. The product, 168 g, was a light orange liquid which was characterized by $^1H$, $^{13}C$ and $^{31}P$ NMR to be a mixture of mono-, di-, and tri-HEMA phosphate and tetraHEMA pyrophosphate.

Filler A

Zirconia Filler Surface-Treated with 3-Methacryloyloxypropyl Sulfonic Acid

Zirconia Sol (271.012 g) was mixed with isopropyl alcohol (IPA, 270.333 g) for 5 minutes. During this mixing time, AMBERLITE IR-120(Plus) ion-exchange resin was rinsed thoroughly with ethanol and decanted to clean the ion exchange resin. SPMA K-Salt (35.595) was then added to the mixture of zirconia sol and IPA and stirred 5 minutes until dissolved. To the resulting mixture was added the ethanol-rinsed ion-exchange resin in order to convert the SPMA K-Salt to the free acid and to adhere the acid-functional methacrylate (3-methacryloyloxypropyl sulfonic acid) to the surface of the zirconia nanoparticles. The resulting mixture was stirred for 20 minutes at room temperature and was then poured into glass Pyrex trays and allowed to dry for 15 minutes at 90° C. The resulting solid was then broken up with a mortar and pestle to yield a loose, free-flowing powder. The acid-treated zirconia powder was designated Filler A and was found to be easily dispersible (typically with stirring and heating) in common dental resins, e.g., TEGDMA, TEGDMA/BisGMA, etc. It was found that the dispersion could be enhanced with the addition of acid-functional (meth)acrylates to the resin mixture after the initial dispersion of the filler into the resin.

Examples 1-4 and Comparative Examples 1-6

Self-Etching Adhesive Compositions

Self-etching adhesive compositions were prepared by mixing the components shown in Table 1. The resulting compositions were designated Examples 1-4 and Comparative Examples (CE) 1-6.

TABLE 1

Self-Etching Adhesive Compositions with and without EDMOA

| Component (Wt.-%) | Ex. 1 | Ex. 2 | Ex. 3 | Ex. 4 | CE-1 | CE-2 | CE-3 | CE-4 | CE-5 | CE-6 |
|---|---|---|---|---|---|---|---|---|---|---|
| Filler A | 20.18 | 20.31 | 20.98 | 21.22 | 20.13 | 20.16 | 20.07 | 20.21 | 19.94 | 21.04 |
| TEGDMA | 24.8 | 24.95 | 16.94 | 17.13 | 33.82 | 33.63 | 33.72 | 33.96 | 33.5 | 16.99 |
| TMP TMA | 10.12 | 10.18 | 9.99 | 10.09 | 0 | 0 | 0 | 0 | 0 | 10 |
| PEG DMA | 5.05 | 5.08 | 0 | 0 | 0 | 0 | 0 | 0 | 0 | 0 |
| UDMA | 7.57 | 7.62 | 9.99 | 10.14 | 12.58 | 12.51 | 12.55 | 12.63 | 12.46 | 10.05 |
| MHP | 8.96 | 8.89 | 9.99 | 10.14 | 8.96 | 8.91 | 8.93 | 8.99 | 8.87 | 10.05 |
| HEMA-P | 21.52 | 21.58 | 29.03 | 29.31 | 22.35 | 22.22 | 22.28 | 22.44 | 22.13 | 29.09 |
| CPQ | 0.91 | 0.91 | 1.51 | 1.51 | 0.88 | 0.49 | 0.68 | 0.49 | 0.87 | 1.51 |
| EDMOA | 0.10 | 0.10 | 0.15 | 0.15 | 0 | 0 | 0 | 0 | 0 | 0 |
| EDMAB | 0.50 | 0 | 1.00 | 0 | 0.97 | 1.94 | 1.47 | 0.98 | 1.94 | 1 |
| DPIHFP | 0.41 | 0.41 | 0.40 | 0.4 | 0.3 | 0.29 | 0.3 | 0.3 | 0.29 | 0.4 |
| TOTAL: | 100 | 100 | 100 | 100 | 100 | 100 | 100 | 100 | 100 | 100 |

Examples 5-10 and Comparative Examples 7-10

Self-Etching Adhesive Compositions and Gel-Time Evaluations

Self-etching adhesive compositions were prepared by mixing the components shown in Table 2 with Stock Mixture A that was made by combining the following ingredients in the amounts indicated:

| Stock Mixture A | |
|---|---|
| Component | Amount (grams) |
| Filler A | 42.035 |
| TEGDMA | 33.916 |
| TMP TMA | 20.013 |
| UDMA | 20.010 |
| MHP | 20.010 |
| HEMA-P | 58.014 |
| CPQ | 3.0070 |
| DPIHFP | 0.7999 |

The resulting compositions including the amounts of each ingredient are shown in Table 2 and were designated Examples 5-10 and Comparative Examples (CE) 7-10. The amounts in grams of the electron donors were determined in such a way as to be molar equivalents.

Gel times of the Compositions listed in Table 2 were determined by estimating the time (to the nearest 5 seconds) that was required for a given mixed composition (electron donor+Stock Mixture A) to transform into a semi-hard to hard solid. The fastest curing samples (Examples 5-6 and 9-10) were light cured and immediately prodded with a wooden spatula to qualitatively rate hardness of the sample.

In order of decreasing hardness were Example 9, Example 6, Example 10, and Example 5.

It can be concluded from the results of this experiment that the most efficient electron donors for use in initiator systems of free-radically polymerizable compositions [e.g., (meth)acrylate containing compositions that include a sensitizer (CPQ) and an iodonium salt (DPIHFP)] are in the polycyclic aromatic classes of anthracenes and biphenylenes.

TABLE 2

Self-Etching Adhesive Compositions with Various Electron Donor Compounds

| Example | Electron Donor | Donor Amount (mg) | Stock Mixture A Amount (g) | Gel Time (seconds) |
|---|---|---|---|---|
| 5 | 2-Ethyl-9,10-dimethoxyanthracene (EDMOA) | 5.1 | 5.0331 | 5 |
| 6 | 1,4-Dimethoxyanthracene | 4.4 | 4.9911 | 5 |
| 7 | Anthracene | 3.3 | 4.9977 | 15-20 |
| 8 | 9,10-Dimethylanthracene | 3.6 | 5.0012 | 15-20 |
| 9 | Biphenylene | 2.6 | 5.0085 | 5 |
| 10 | 9-Methylanthracene | 3.7 | 5.0012 | 5 |
| CE-8 | EDMAB | 3.8 | 5.0130 | >40 |
| CE-9 | 1,2,4-Trimethoxybenzene | 3.1 | 5.0816 | >40 |
| CE-10 | 2,7-Dimethoxynapthalene | 3.4 | 5.0126 | >40 |

Evaluation A

Photo-DSC Evaluations

Each sample was evaluated for rate and extent of cure by photo differential scanning calorimetry (photo-DSC) using a model DSC2920 calorimeter (available from TA Instruments, New Castle, Del.) with light from a 100 W medium pressure mercury that was filtered through a Model GG400 long pass filter (available from Esco Products, Oak Ridge, N.J.).

Figure 1:
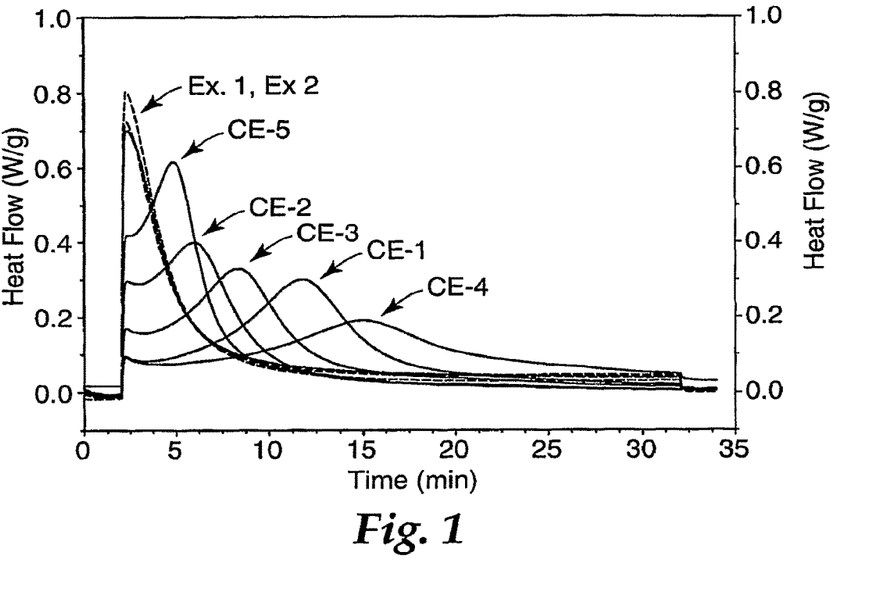
FIG. 1 is a graph showing photo-DSC (Differential Scanning Calorimetry) evaluation of Examples 1-2 and Comparative Examples 1-5.

Examples 1-2 and Comparative Examples 1-5 were subjected to Photo-DSC and the results provided in FIG. 1. The graphs from FIG. 1 clearly show that Examples 1-2 (adhesive compositions which contain EDMOA as part of the photoinitiator system) show substantially improved cure efficiency over Comparative Examples 1-5 (which do not contain EDMOA). It is also observed from FIG. 1 that cure rates of the Comparative Examples are enhanced with increasing amounts of EDMAB in the compositions. However, high levels of amines, such as EDMAB, are often unacceptable in terms of performance of self-etching adhesive compositions.

Evaluation B

Curing and Photo-DSC Evaluations

Examples 3-4 and Comparative Example 6 were evaluated for bench-top cure by placing 8 drops of adhesive composition into a dental mixing well and curing for 10 seconds with an XL 3000 curing light (3M Company, St. Paul, Minn.). The following results were observed:

Example 3—Cured to hard solid; Example 4—Cured to hard solid; and Comparative Example 6—Very slight cure to "stringy" semi-solid to liquid material. Thus, improved cure was observed for Examples 3-4 (adhesive compositions which contain EDMOA as part of the photoinitiator system) as compared to Comparative Example 6 (which does not contain EDMOA).

Figure 2:
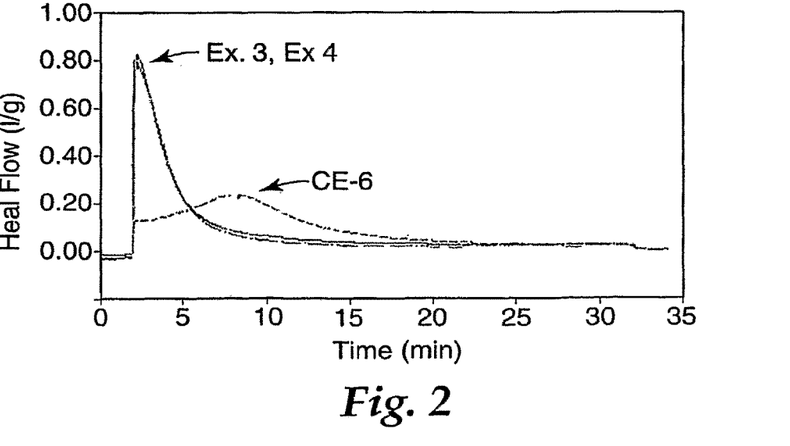
FIG. 2 is a graph showing photo-DSC evaluation of Examples 3-4 and Comparative Example 6.

Examples 3-4 and Comparative Example 6 were also subjected to Photo-DSC and the results provided in FIG. 2. The graphs from FIG. 2 clearly show that Examples 3-4 show substantially improved cure efficiency over Comparative Example 6.

Evaluation C

Bond Strength Evaluations

Shear bond strengths of adhesive test samples were carried out according to the Notched Edge Shear Adhesive Test Method (Uncut Enamel, Cut Enamel, or Dentin) and Wire-Loop Shear Adhesive Test Method (Cut Enamel or Dentin) described herein. Bond strengths were measured initially after overnight storage at room temperature. Results are shown in Table 3.

The data from Table 3 show that Example 3 (self-etching adhesive composition which contains both the non-acid reactive electron donor EDMOA and the tertiary amine EDMAB as part of the photoinitiator system) provided the highest overall bond strength performance.

TABLE 3

Shear Bond Strengths

| Example | Test Method | Substrate | Bond Strength (MPa) |
|---|---|---|---|
| 3 | Notched Edge Shear | Uncut Enamel | 33.73 |
| 3 | Notched Edge Shear | Cut Enamel | 30.25 |
| 3 | Notched Edge Shear | Dentin | 34.17 |
| 3 | Wire Loop | Cut Enamel | 28.00 |
| 3 | Wire Loop | Dentin | 23.10 |
| 4 | Notched Edge Shear | Uncut Enamel | 25.61 |
| 4 | Notched Edge Shear | Cut Enamel | 31.86 |
| 4 | Notched Edge Shear | Dentin | 19.06 |
| 4 | Wire Loop | Cut Enamel | 18.20 |
| 4 | Wire Loop | Dentin | 6.00 |
| CE-6 | Notched Edge Shear | Uncut Enamel | 24.63 |
| CE-6 | Notched Edge Shear | Cut Enamel | 33.78 |
| CE-6 | Notched Edge Shear | Dentin | 31.90 |
| CE-6 | Wire Loop | Cut Enamel | 28.20 |
| CE-6 | Wire Loop | Dentin | 21.60 |

An additional evaluation was conducted with immediate bond strengths on cut enamel using the Notched Edge Shear Test Method, except that the samples were broken immediately after preparation. Results are shown in Table 4.

The data from Table 4 again show that Example 3 (self-etching adhesive composition which contains both EDMOA and EDMAB) provided the highest bond strength performance.

TABLE 4

Shear Bond Strengths

| Example | Test Method | Substrate | Bond Strength (MPa) |
|---|---|---|---|
| 3 | Notched Edge Shear | Cut Enamel | 22.50 |
| 4 | Notched Edge Shear | Cut Enamel | 10.11 |
| CE-6 | Notched Edge Shear | Cut Enamel | 19.35 |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A polymerizable dental composition comprising
free-radically polymerizable components including a
free-radically polymerizable acidic component comprising a monomer, oligomer, or polymer comprising acid functionality selected from the group consisting of phosphate, phosphonic acid, bisphosphonic acid, combinations thereof, and anhydrides thereof;
a photoinitiator system comprising
an amine electron donor,
a polycyclic aromatic electron donor component selected from unsubstituted anthracene and biphenylene and alkyl, alkoxy, aryl, and aryloxy substituted derivatives of anthracene, and
a visible light sensitizer selected from the group consisting of monoketones, diketones, and alpha diketones, that absorb some light within a range of 400 nm to 520 nm, wherein the visible light sensitizer is different from the polycyclic aromatic electron donor compound.

2. The composition of claim 1, wherein the polycyclic aromatic component is selected from the group consisting of 2-ethyl-9,10-dimethoxyanthracene (EDMOA), 1,4-dimethoxyanthracene, 9-methyl anthracene, 9,10-methylanthracene, and combinations thereof.

3. The composition of claim 1, wherein the free-radically polymerizable acidic component comprises an ethylenically unsaturated component.

4. The composition of claim 3, wherein the ethylenically unsaturated component comprises a phosphorylated (meth)acrylate.

5. The composition of claim 1, wherein the amine electron donor is a tertiary amine.

6. The composition of claim 5, wherein the tertiary amine comprises ethyl-4-dimethylamino benzoate (EDMAB).

7. The composition of claim 1, further comprising a free-radically polymerizable non-acidic component.

8. The composition of claim 1, wherein the visible light sensitizer comprises camphorquinone (CPQ).

9. The composition of claim 1, wherein the photoinitiator system further comprises an iodonium salt.

10. The composition of claim 1, further comprising a filler.

11. The composition of claim 10, wherein the filler comprises nanoparticles.

12. A polymerizable dental composition comprising
free-radically polymerizable components including a
free-radically polymerizable component comprising phosphorylated functionality, and
a photoinitiator system comprising:
an amine electron donor; and
a polycyclic aromatic electron donor compound, wherein the polycyclic aromatic component is selected from unsubstituted anthracene and biphenylene and alkyl, alkoxy, aryl, and aryloxy substituted derivatives of anthracene, and
a visible light sensitizer selected from the group consisting of monoketones, diketones, and alpha diketones, that absorb some light within a range of 400 nm to 520 nm, wherein the visible light sensitizer is different from the polycyclic aromatic electron donor compound.

13. The composition of claim 12, wherein the polycyclic aromatic component is selected from the group consisting of 2-ethyl-9,10-dimethoxyanthracene (EDMOA), 1,4-dimethoxyanthracene, 9-methyl anthracene, 9,10-methylanthracene, and combinations thereof.

14. The composition of claim 12, wherein the free-radically polymerizable component comprises an ethylenically unsaturated component.

15. The composition of claim 14, wherein the ethylenically unsaturated component comprises a non-acidic (meth)acrylate.

16. The composition of claim 14, wherein the ethylenically unsaturated component comprises a phosphorylated (meth)acrylate.

17. The composition of claim 12, wherein the amine electron donor is a tertiary amine.

18. The composition of claim 17, wherein the tertiary amine comprises ethyl-4-dimethylamino benzoate (EDMAB).

19. The composition of claim 12, wherein the visible light sensitizer comprises camphorquinone (CPQ).

20. The composition of claim 12, wherein the photoinitiator system further comprises an iodonium salt.

21. The composition of claim 12, further comprising a filler.

22. The composition of claim 21, wherein the filler comprises nanoparticles.

23. The composition of claim 1, wherein the monomer, oligomer, or polymer comprising acid functionality is present in an amount of at least 30% by weight of the total composition.

* * * * *

UNITED STATES PATENT AND TRADEMARK OFFICE
CERTIFICATE OF CORRECTION

PATENT NO. : 9,993,393 B2
APPLICATION NO. : 12/159250
DATED : June 12, 2018
INVENTOR(S) : Bradley Craig et al.

Page 1 of 1

It is certified that error appears in the above-identified patent and that said Letters Patent is hereby corrected as shown below:

In the Drawings

Sheet 1,
Y-axis, Fig. 2, delete "Heal" and insert -- Heat --, therefor.

In the Specification

Column 6,
Line 3, delete "bisphenolA" and insert -- bisphenol A --, therefor.

Column 13,
Line 53, delete "unimodial" and insert -- unimodal --, therefor.

Column 13,
Line 54, delete "polymodial" and insert -- polymodal --, therefor.

Column 17,
Line 45, delete "than" and insert -- then --, therefor.

Column 19,
Line 5, After "procedure" insert -- . --.

Column 23,
Line 28, (Approx.) (Table 2.), "Dimethoxynapthalene" and insert -- Dimethoxynaphthalene --, therefor.

In the Claims

Column 25,
Line 29, In Claim 2, delete "methyl anthracene," and insert -- methylanthracene, --, therefor.

Signed and Sealed this
Nineteenth Day of February, 2019

Andrei Iancu
*Director of the United States Patent and Trademark Office*